(12) United States Patent
Champseix et al.

(10) Patent No.: US 8,308,656 B2
(45) Date of Patent: Nov. 13, 2012

(54) SAMPLING DEVICE AND METHOD USABLE IN AN ANALYSIS AUTOMATED DEVICE

(75) Inventors: Henri Champseix, Saint Gely du Fesc (FR); Serge Champseix, Tarnac (FR); Jean-Pierre Milhat, Carnon (FR)

(73) Assignee: C2 Diagnostics, Montpellier (FR)

( * ) Notice: Subject to any disclaimer, the term of this patent is extended or adjusted under 35 U.S.C. 154(b) by 293 days.

(21) Appl. No.: 12/374,846

(22) PCT Filed: Jul. 26, 2007

(86) PCT No.: PCT/FR2007/001293
§ 371 (c)(1),
(2), (4) Date: Jan. 23, 2009

(87) PCT Pub. No.: WO2008/012445
PCT Pub. Date: Jan. 31, 2008

(65) Prior Publication Data
US 2009/0259144 A1 Oct. 15, 2009

(30) Foreign Application Priority Data

Jul. 26, 2006 (FR) ...................................... 06 06844

(51) Int. Cl.
*A61B 5/15* (2006.01)
*G01N 1/10* (2006.01)
*A61M 1/00* (2006.01)

(52) U.S. Cl. ........ 600/577; 600/573; 600/576; 600/579; 141/1; 422/547; 422/550; 422/570; 436/180; 604/321; 604/403

(58) Field of Classification Search ................. 600/573, 600/576, 577, 579; 141/1; 422/547, 550, 422/570; 436/180; 604/321, 403
See application file for complete search history.

(56) References Cited

U.S. PATENT DOCUMENTS

| | | | |
|---|---|---|---|
| 4,342,341 A * | 8/1982 | Lee | 141/1 |
| 4,586,546 A * | 5/1986 | Mezei et al. | 141/2 |
| 6,274,087 B1 | 8/2001 | Preston et al. | |
| 6,360,794 B1 | 3/2002 | Turner | |
| 7,128,105 B2 * | 10/2006 | Tribble et al. | 141/319 |

FOREIGN PATENT DOCUMENTS

| | | |
|---|---|---|
| FR | 2 767 583 | 2/1999 |
| WO | 97/14967 | 4/1997 |

* cited by examiner

*Primary Examiner* — Sean Dougherty
(74) *Attorney, Agent, or Firm* — Young & Thompson

(57) ABSTRACT

A sampling device includes a body, a needle, a sealing element and an element for feeding and removing a liquid. The needle has at least one groove located between the sealing element and the sampling end of the needle. The sampling end has a sampling hole opening out on a lateral wall of the end. The sampling device leakage problems encountered in the conventional art to be overcome while at the same time resolving the problems of placing the inside of a tube containing a product to be analyzed at atmospheric pressure.

20 Claims, 5 Drawing Sheets

SAMPLING DEVICE AND METHOD USABLE IN AN ANALYSIS AUTOMATED DEVICE

BACKGROUND OF THE INVENTION

Field of the Invention

The present invention relates to a sampling device which can be used in an analysis automated device. It also relates to a process for taking samples and/or sampling implementing a device according to the invention.

DESCRIPTION OF THE CONVENTIONAL ART

The field of the invention is the field of sampling automated and/or injection devices and more particularly analysis automated devices.

In general, tubes containing products to be analyzed which are used in analysis automated devices are tubes with a stopper, usually made of elastomer. These tubes are increasingly placed under a relative vacuum in order to facilitate the filling of these tubes. For example, when taking blood samples, tubes are used in which a relative vacuum is created to avoid the use of a syringe. In analysis automated devices, sampling and injection operations are carried out by passing a suitable needle through the stopper without removing the stopper from these tubes. Now, the differences in pressure between the inside and the outside of the tube cause difficulties when sampling the product contained in these tubes. Moreover, when the needle passes through the stopper, the deformations of the stopper and the penetration of the needle into the tube increase the pressure fluctuations in these tubes.

All of these variations in pressure can reduce the accuracy of the quantities taken from or injected into these tubes. Current systems and devices recommend the use of specific needles to try to resolve these problems. Thus, the patent FR 2 767 583 proposes the use of a needle having a cutting tip on the one hand and a slot, hollow or groove on its external surface on the other, allowing the inside of the tube to be placed at atmospheric pressure by the circulation of air between the outside and the inside of the tube thanks to the groove.

However, such a needle poses several problems. Firstly, the presence of a groove on its outside surface poses risks of leakage of the product handled during a sampling operation. Secondly, the cutting tip of the needle poses a risk to the operators required to handle it that they may be pricked by it.

Moreover, sampling automated devices have feed circuits for diluents used during the analysis of a sample taken or for products intended to clean the needle. Such cleaning operations are frequent and are of prime importance in order not to contaminate the products to be analyzed by each other or by analysis products. Now, the use of a needle with a groove on its outside surface, such as that described in the patent FR 2 767 583, poses the problems of leaking via this slot of the diluent on the one hand and of the product intended to clean the needle on the other.

SUMMARY OF THE INVENTION

An aim of the invention is to propose a sampling device which allows the leakage problems described above to be overcome while at the same time resolving the problems of placing the inside of the tube at atmospheric pressure.

An aim of the invention is to propose a sampling and/or injection device which poses less danger of pricking the operator than the current devices.

The invention proposes to deal with the above-mentioned problems by a sampling device which can be used in an automatic analysis device, this device comprising:
  a body,
  a sampling needle that can move in the body between an extended position suitable for taking a sample and a retracted position, the needle having a sampling end and at least one groove extending longitudinally over its outside surface, and
  sealing means between the body and said outside surface of the needle; the groove extending between the sealing means and the sampling end regardless of the position of the needle between its extended position and its retracted position. Through the combined use of at least one groove on the outside surface of a needle and sealing means, the device according to the invention advantageously provides solutions:
  on the one hand to the problems of accuracy with regard to the quantities sampled or injected by the needle by placing under atmospheric pressure the internal volume of the tube in which the sampling (and/or injection) is (are) carried out; and
  on the other hand to the problems of leakage of dilution product or cleaning products via the groove.

In a particular embodiment of the device according to the invention, the needle can have at least one second groove arranged such that in the retracted position the sealing means are arranged between the first and the second groove, said first and second grooves each defining a respective grooved zone and a sealing zone between them.

In fact, to ensure that a sampling will be carried out in the tube even if it contains little product, the needle is moved close to the bottom of the tube. Thus, it may be that the first groove has penetrated the tube beyond the stopper, no longer ensuring the circulation of air. This is not generally a problem, because the volumes sampled are small. However, if it is desired to sample a greater quantity, the second grooved zone, provided to pass through the stopper in the extended position, then allows the circulation of air to resume.

Of course, the needle can have several grooved zones, separated from each other by a respective sealing zone.

Advantageously, the device according to the invention can have several grooves on its outside surface, the number of grooves being able to be determined depending on the sought use.

The dimensions of the groove, and more particularly the length and the depth of the groove must be such that, when the stopper is pierced, the deformation of the latter does not block the groove and thus does not prevent the internal volume of the tube from being placed at atmospheric pressure.

In a particular embodiment, the groove can have a rectangular, triangular, rounded or trapezoidal or even dovetail section, each of these sections having its own technical effects. For example, a rounded section facilitates the cleaning of the needle and more particularly of the grooves, whereas a square, rectangular or also trapezoidal section allows a more effective application of atmospheric pressure. Moreover, each of the sections presents lesser or greater production problems.

The sealing means are placed in an internal volume of the body of the device according to the invention. Thus, in a way, they allow the internal volume of the body to be divided into two parts:
  one part, termed downstream, corresponding to the part of internal volume situated beyond the sealing means in the direction of the sampling end of the needle and, one part, termed upstream, corresponding to the remainder of the internal volume of the body.

The task of the sealing means is to produce the seal between the downstream part and the upstream part. They are arranged so as to be in contact with the outside surface of the needle on the one hand and with an inside surface of the body of the device on the other. The contact between the sealing means and the needle is adjusted such that the needle can slide along it.

The sealing means can advantageously include at least one sealing ring.

The sealing means can advantageously rest on at least one shoulder of the body. The sealing means can also be mounted, clamped or not, between two shoulders or a slot, or shapes which project into the internal volume of the body of the device.

Advantageously, the device according to the invention can moreover comprise means (122) for feeding and/or means (121) for removing a given liquid in the volume downstream of the body of the device according to the invention. These means can comprise at least one circuit feeding and one circuit removing the given liquid. In a particular version of the device according to the invention, the feed circuit and the removal circuit can have parts in common. The feed and/or removal means can moreover comprise means for pushing or aspirating a liquid in the feed and/or removal circuits, such as pumps, valves. These means can moreover comprise means for blocking the feed and/or removal circuits when these circuits are not in use.

In a particular version of the device according to the invention, the fed liquid can comprise a liquid under pressure.

In another particular version of the device according to the invention, the fed and/or evacuated liquid can comprise a cleaning product and/or a product for rinsing the needle. In this particular configuration, the device according to the invention can be placed above a cleaning tank provided to recover part of the product during a rinsing and/or cleaning operation. In this configuration, the needle is preferably located in a retracted position so that the cleaning and/or rinsing product comes directly into contact with the downstream part of the needle to be cleaned and/or rinsed.

According to another particular version of the device according to the invention, the liquid can comprise a dilution product intended to be added to a vessel containing a sample taken from a tube with a view to submitting it to various analyses.

The liquid can also comprise a test reagent potentially intended to react with the sample taken within the scope of an analysis.

Advantageously, on the side of the sampling end of the needle, the groove ends at a distance from said end. This distance can be a function of the shape of the sampling end, as well as of the dimensions of the end, and such that the sampling end is sufficiently resistant to pass without being damaged through the stopper of the tube containing the product to be analyzed. The stress exerted on the needle during the piercing of the stopper must not damage the needle.

In a particular version of the device according to the invention, the sampling end of the needle can be rounded. Such a rounded end allows to reduce the risks of an operator being pricked by the needle when he is required to use it.

However, in another particular version of the device according to the invention, the end of the needle can be pointed, and more particularly the needle can have a sampling end with a cutting edge, this cutting edge being connected to the substantially cylindrical body of the needle by at least one or more faces, at least one of these faces having a sampling hole.

Advantageously, the sampling end of the needle can have at least one hole opening out laterally on the surface of the needle. Such a hole thus makes it possible, firstly to prevent a piece from being cut from the stopper of a tube during perforation of this stopper, and secondly the blocking of the needle by the piece cut from the stopper, which is the case in the majority of needles in the prior art having a hole at the end of the needle. Moreover, such a hole allows a greater accuracy with regard to the quantity of the product sampled by the device according to the invention.

Surprisingly, it appears that the grooves of the needle improve the cleaning performance in respect of this needle.

According to another feature of the invention, a method which uses the device according to the invention is proposed.

BRIEF DESCRIPTION OF THE DRAWING FIGURES

Other advantages and characteristics will become apparent on examination of the detailed description of an embodiment that is in no way limitative, and the attached drawings in which.

DETAILED DESCRIPTION OF THE INVENTION

The example described above is a particular non-limitative application of a device according to the invention.

Figure 1:
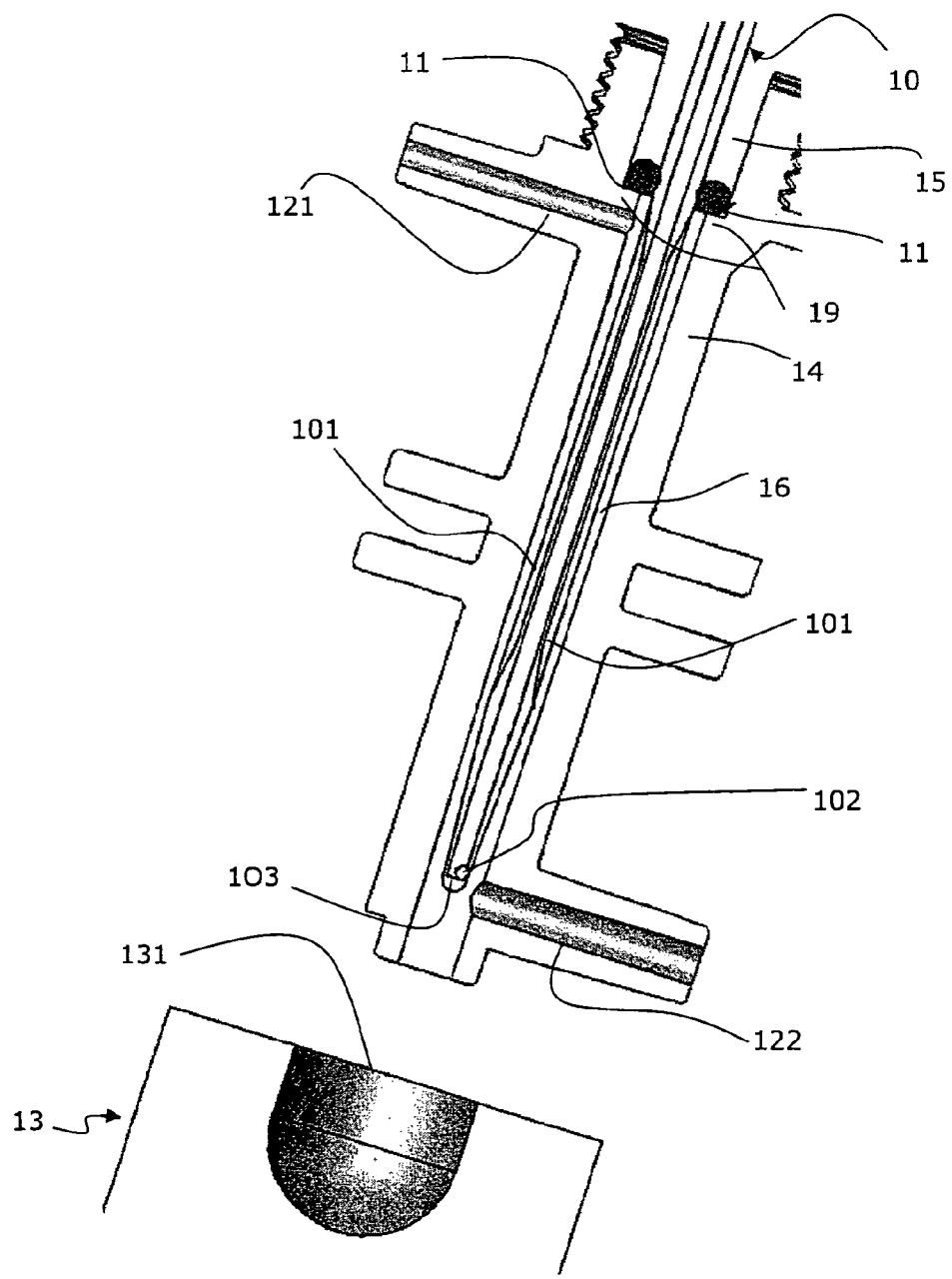
FIG. 1 is a diagrammatic section representation of a device according to the invention, the sampling needle of the device being in a retracted position.

FIG. 1 is a diagrammatic section representation of a sampling device according to the invention comprising a body 14, a needle 10, sealing means 11, and means 121 and 122 for feeding and removing a liquid in the internal volume of the body 14 of the device. The sampling needle 10 is provided with a sampling end 103. Partially represented on FIG. 1 is a tube 13 having a stopper 131. In this figure, the sampling needle is in a retracted position, i.e. the sampling end 103 is located inside the body 14.

In addition, this needle 10 has two grooves 101 on its outside surface and a hole 102. The grooves 101 are located between the sealing means 11 and the sampling end 103 of the needle 10. Indeed, the grooves 101 do not extend over the whole length of the needle and are present only on a limited part of the needle 10. This limited part is located between the sampling end 103 and the sealing means 11 regardless of the position of the needle between the retracted position represented in this FIG. 1 and the extended position allowing a sample intended for analysis to be taken (see FIGS. 2A and 2B). The grooves 101 are therefore located beyond the sealing means in the direction of the sampling end 103.

The sealing means 11 are placed in an internal volume of the body 14 of the device according to the invention. They allow the internal volume of the body 14 to be divided into two parts:
- one part 16, termed downstream, corresponding to the part of the internal volume of the body 14 situated beyond the sealing means 11 in the direction of the sampling end 103 of the needle 10 and,
- one part 15, termed upstream, corresponding to the remainder of the internal volume of the body 14.

The task of the sealing means 11 is to create the seal between the downstream part 16 and the upstream part 15. They are arranged so as to be in contact with the outside surface of the needle 10 on the one hand and with an inside surface of the body 14 of the device on the other. The contact between the sealing means 11 and the needle 10 is adjusted so that the needle 10 can slide along it.

In the particular example described here, the sealing means constitute a sealing ring. The sealing ring rests on a shoulder 19 of the body 14 of the device.

The device also has a feed circuit 122 and a removal circuit 121 for a given liquid in the downstream part 16. The device can also have means for pushing or for aspirating (not shown) a product in the feed and/or removal circuits, such as pumps and valves. In addition, these means can comprise means for blocking the feed circuit 122 and/or the removal circuit 121 when they are not in use. Of course, in another embodiment, the circuit 121 can serve as a feed circuit for a liquid in the downstream part and the circuit 122 as a removal circuit for this liquid.

The liquid fed into the downstream part 16 can be under pressure. It can be a cleaning product or a dilution product. In the case where the liquid fed by the feed circuit 122 is a cleaning product, the device is placed above a reception tank (not shown) provided to receive all or part of the cleaning product. The cleaning product can also be removed by the removal circuit 121 creating a vacuum at the downstream part 16 of the internal volume of the body. In the case where the liquid fed by the feed circuit 122 is a diluent product the device is placed above a vessel (not shown) intended to receive the product in question. The task of the sealing means 11 is to ensure the sealing of the downstream part 15 of the internal volume of the body 14 of the device vis-à-vis products fed by the feed means 122 in the downstream part.

Figure 2A:
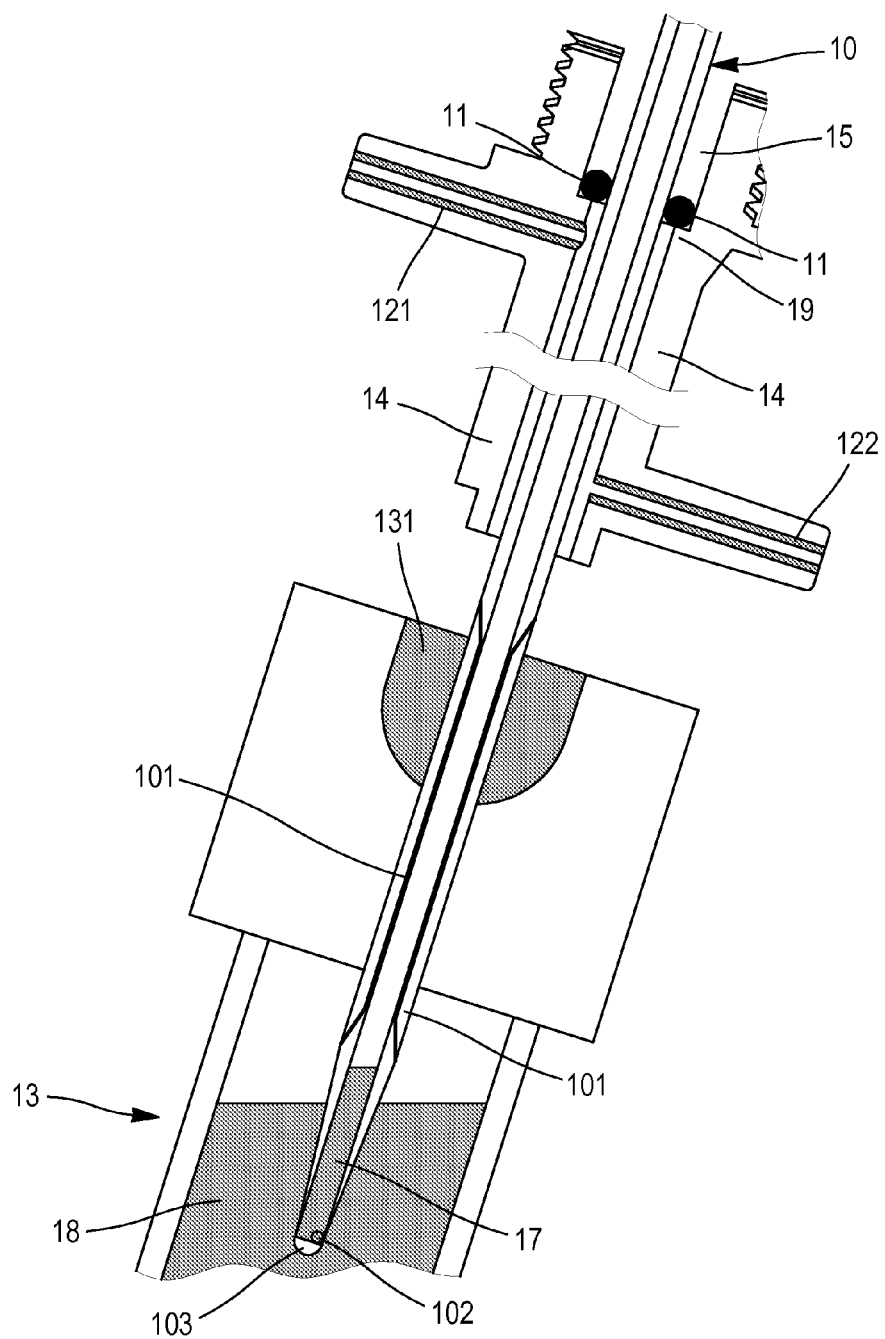
FIG. 2A is a diagrammatic section representation of a device according to the invention, the sampling needle of the device being in an extended position.

In FIG. 2A, the device according to the invention is shown with the sampling needle 10 in an extended position. More precisely, the needle 10 is shown after perforation of the stopper 131 of the tube 13 by the needle 10. During the perforation of the stopper 131 of the tube 13, the inside of the tube 13 is placed at atmospheric pressure by the circulation of air through the grooves 101.

Moreover, the needle 10 has a sampling hole 102 on the lateral wall of the sampling end 103 and near the tip of this end 103. The positioning of this hole 102 makes it possible, firstly to prevent a piece from being cut from the stopper 131 of a tube 13 during the perforation of this stopper and the blocking of the hole 102 with the piece in question, and secondly to take a sample 17 of the product 18 to be analyzed with great accuracy with regard to the quantity sampled in the needle 10.

The grooves 101 end at a distance from the sampling end 103. This distance can be a function of the shape of the sampling end 103 as well as of the dimensions of the end 103 and such that the sampling end 103 is sufficiently resistant to pass without being damaged through the stopper 131 of the tube 13 containing the product 18 to be analyzed. The stress exerted on the needle 10 during the piercing of the stopper must not damage the needle 10.

Figure 2B:
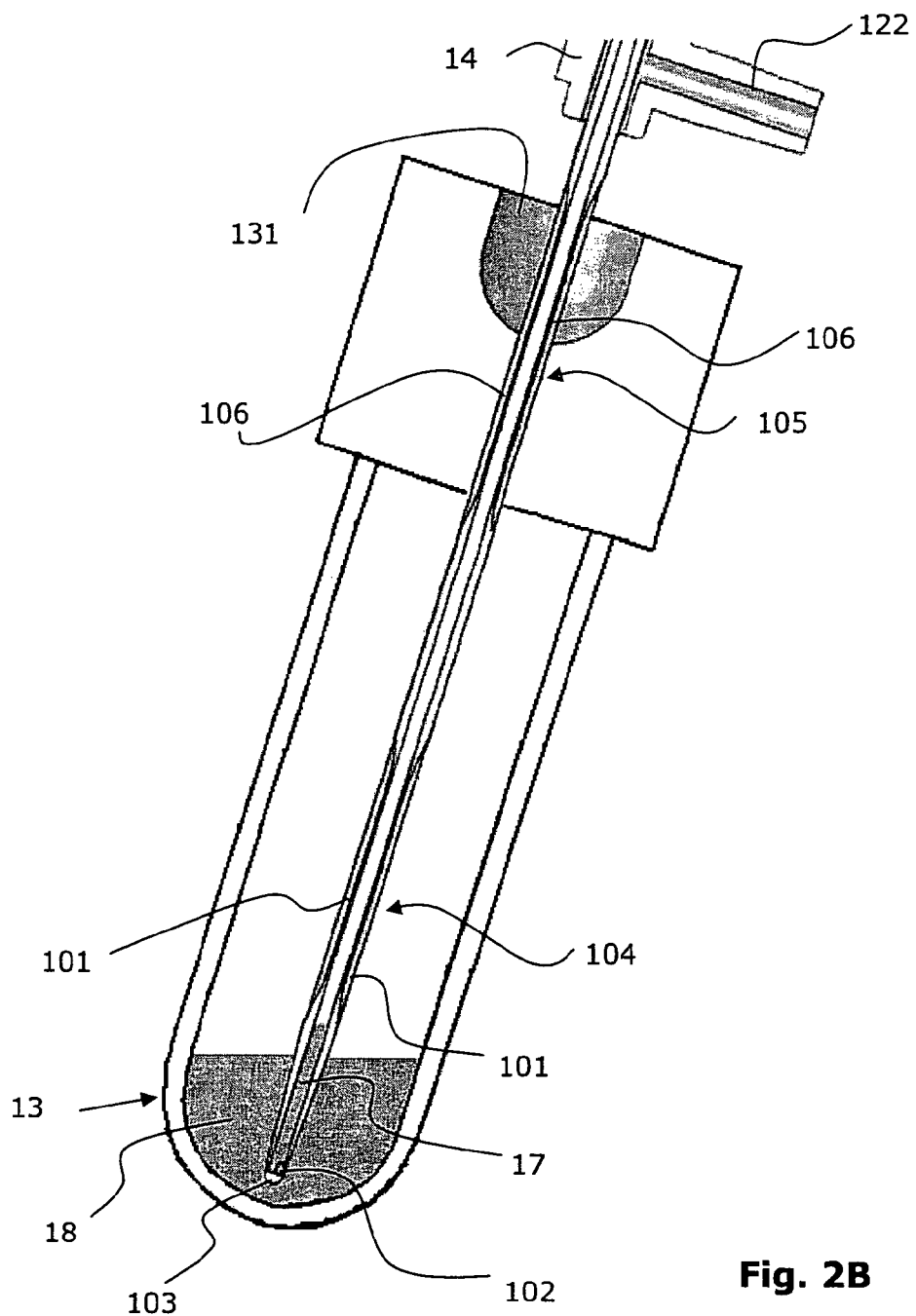
FIG. 2B is a diagrammatic section representation of a device according to the invention, the sampling needle of the device having two grooved zones and being in an extended position.

FIG. 2B is a diagrammatic section representation of a device according to the invention. In FIG. 2B, the sampling needle 10 is in a sampling position. The sampling end 103 of the needle 10 is located close to the bottom of the tube 13 containing the product 18 to be sampled. The needle 10 has two grooved zones 104 and 105. The first grooved zone 104 allows the inside of the tube 13 to be placed at atmospheric pressure during the piercing of the stopper 131 of the tube 13 by the needle 10. The second grooved zone 105, comprising the grooves 106, passes through the stopper of the tube 13 in order to allow a circulation of air between the inside and the outside of the tube 13 so as to avoid the vacuum created by the sampling of a large quantity of product 18. When the needle 10 is in its retracted position, the sealing means are arranged between the first grooved zone 104 and the second grooved zone 105.

Figure 3:
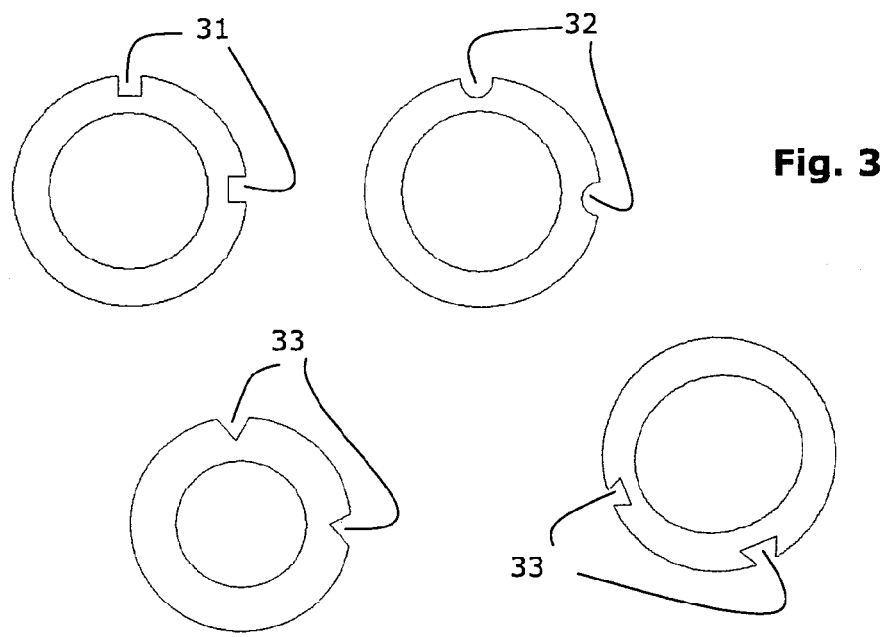
FIG. 3 is a diagrammatic section representation of four needles having grooves with different sections, which can be used in the device according to the invention.

As shown in FIG. 3, the needle 10 can have grooves 31 with a square or rectangular section, grooves 32 with a circular section, grooves 33 with a triangular section, and/or grooves 34 with a trapezoidal and more particularly dovetail section. Each of these sections has its own technical effects. For example, a rounded section facilitates the cleaning of the needle and more particularly of the grooves, whereas a square, rectangular or also trapezoidal section allows atmospheric pressure to be created more effectively to the inside of the tube 13.

Figure 4:
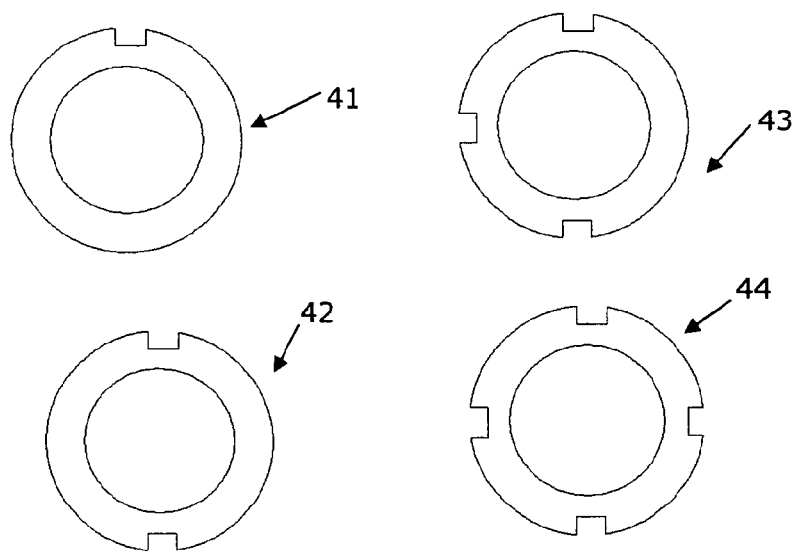
FIG. 4 is a diagrammatic section representation of four needles, each having a different number of grooves, which can be used in the device according to the invention.

FIG. 4 is a diagrammatic representation of a needle 41 having a single groove. Also shown in FIG. 4 is a needle 42 having 2 grooves, a needle 43 having 3 grooves and a needle 44 having 4 grooves.

Figure 5:
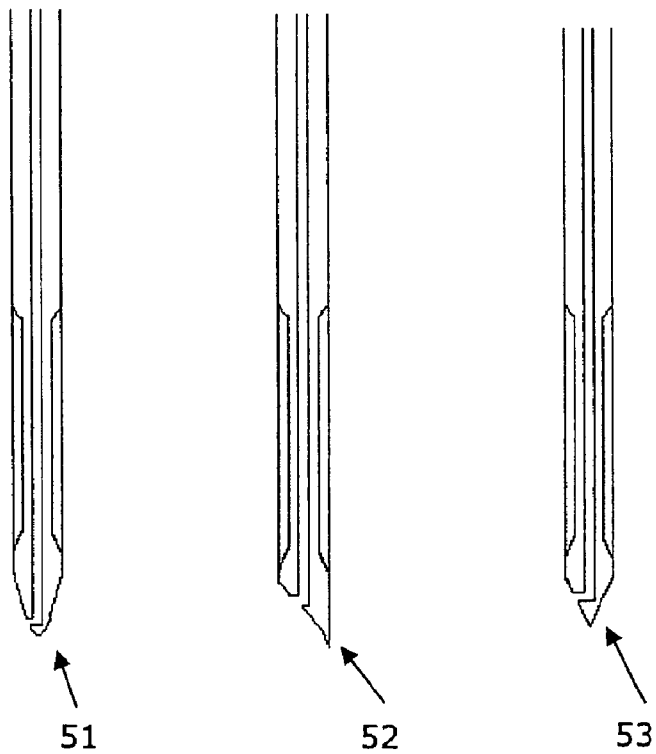
FIG. 5 is a diagrammatic section representation of three needles, each having a sampling end with a different shape.

Moreover, the sampling end 103 of the needle 10 can have a rounded shape 51 as shown in FIG. 5. Such a rounded end 51 allows to reduce the risk of an operator being injured, and more particularly being pricked, by the needle when he is required to handle it.

However, in a particular version of the device according to the invention, the end of the needle can have a pointed shape 52 and 53. More particularly, the needle can have a sampling end with a cutting edge, this cutting edge being connected to the substantially cylindrical body of the needle by at least one or more faces, at least one of these faces having a sampling hole.

Of course, the device according to the invention is not limited to the example just described. The number, arrangement and shape of the grooves of the needle can vary. The needle can have a sampling end with a section that is different from those described within the scope of the description of the particular example above. The sampling needle can be moved in a circular motion. The sealing means can be fixed by means of a slot or several shoulders. Finally, the sampling needle can have several sampling holes.

The invention claimed is:

1. A sampling device which can be used in an analysis automated device, said device comprising:
   a body (14),
   a sampling needle (10) having a sampling end (103), that can move in the body (14) between an extended position suitable for taking a sample (17) in a tube (13), in which the sampling end (103) is outside of the body (14), and a retracted position in which the sampling end (103) is located inside the body (14), said needle (10) having at least one groove (101) extending longitudinally over an outside surface of the needle (10) in a grooved zone of said needle, and a seal (11) between the body (14) and said outside surface of the needle (10);

the seal (11) being arranged in a sealing zone of the needle (10) at least when the needle is in the retracted position, the seal (11) and the groove (101) being configured such that said groove (101) extends between said seal (11) and said sampling end (103) regardless of a position of said needle (10) between said extended position and said retracted position of the needle.

2. The device according to claim 1, wherein the needle (10) has at least one second groove (106) arranged such that in the retracted position the sealing means are arranged between said first and second grooves.

3. The device according to claim 2, wherein the needle has several grooved zones separated from each other by respective sealing zones.

4. The device according to claim 2, wherein the seal (11) rests on at least one shoulder (19) of the body (14).

5. The device according to claim 2, wherein the seal (11) includes at least one sealing ring.

6. The device according to claim 3, wherein the seal (11) rests on at least one shoulder (19) of the body (14).

7. The device according to claim 1, wherein the seal (11) rests on at least one shoulder (19) of the body (14).

8. The device according to claim 1, wherein the seal (11) includes at least one sealing ring.

9. The device according to claim 8, wherein on a side of the sampling end (103) of the needle (10), the groove (101) ends at a distance from said end (103).

10. The device according to claim 8, wherein the groove (101) has a rectangular section (31).

11. The device according to claim 1, wherein the device further comprises at least one of means (122) for feeding or means (121) for removing a liquid in an internal volume of the body (14) situated on a side of the sampling end (103) of the needle (10) relative to the seal (11).

12. The device according to claim 11, wherein the liquid comprises at least one of a cleaning and rinsing product.

13. The device according to claim 11, wherein the liquid comprises a dilution product.

14. The device according to claim 11, wherein the liquid comprises a liquid under pressure.

15. The device according to claim 1, wherein the groove (101) has a triangular section (33).

16. The device according to claim 1, wherein the groove (101) has a rounded section (32).

17. The device according to claim 1, wherein the groove (101) has a trapezoidal section (34).

18. The device according to claim 1, wherein the sampling end (103) of the needle (10) is rounded.

19. The device according to claim 1, wherein the sampling end (103) of the needle (10) has at least one hole (102) opening out laterally on the surface of the needle (10).

20. A method for analyzing a sample, or a blood sample, comprising sampling with a sampling device which comprises:

a body (14), a sampling needle (10) having a sampling end (103), that can move in the body (14) between an extended position suitable for taking a sample (17) in a tube (13) in which the sampling end (103) is outside of the body (14), and a retracted position in which the sampling end (103) is located inside the body (14), said needle (10) having at least one groove (101) extending longitudinally over an outside surface of the needle (10) in a grooved zone of said needle (10), and a seal (11) between the body (14) and said outside surface of the needle (10);

the seal (11) being arranged in a sealing zone of the needle (10) at least when the needle (10) is in the retracted position, the seal (11) and the groove (101) being configured such that said groove (101) extends between the seal (11) and said sampling end (103) regardless of a position of said needle (10) between said extended position and said retracted position of the needle (10).

\* \* \* \* \*